(12) United States Patent
Glaros et al.

(10) Patent No.: US 10,591,390 B1
(45) Date of Patent: Mar. 17, 2020

(54) DIRECT CAPTURE AND ANALYSIS OF AEROSOLS AND VAPORS BY PAPER SPRAY MASS SPECTROMETRY

(71) Applicant: U.S. Army Edgewood Chemical Biological Center, APG, MD (US)

(72) Inventors: Trevor G. Glaros, North East, MD (US); John M Nilles, Elkridge, MD (US); Jennifer W Sekowski, Forest Hill, MD (US); Harold S Wylie, North East, MD (US); Elizabeth S. Dhummakupt, Abingdon, MD (US); Phillip M Mach, Edgewood, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 15/813,326

(22) Filed: Nov. 15, 2017

Related U.S. Application Data

(60) Provisional application No. 62/434,671, filed on Dec. 15, 2016.

(51) Int. Cl.
*G01N 1/22* (2006.01)
*H01J 49/04* (2006.01)
*H01J 49/00* (2006.01)

(52) U.S. Cl.
CPC ........ *G01N 1/2273* (2013.01); *H01J 49/0031* (2013.01); *H01J 49/0409* (2013.01); *H01J 49/0422* (2013.01); *H01J 49/0427* (2013.01)

(58) Field of Classification Search
None
See application file for complete search history.

(56) References Cited

U.S. PATENT DOCUMENTS

2013/0344610 A1 * 12/2013 Cooks ................. H01J 49/0431
436/141

FOREIGN PATENT DOCUMENTS

WO    WO-2012170301 A1 * 12/2012 .......... H01J 49/0431

OTHER PUBLICATIONS

Nest Protect teardowns from iFixit.com, sparkfun.com (Year: 2013).*
Lin et al., "Paper spray-MS for bioanalysis" Bioanalysis (2014) 6(2), 1-10 (Year: 2014).*
Lin et al., "Development and applications of paper-based electrospray ionization-mass spectrometry for monitoring of sequentially generated droplets" Analyst. Apr. 7, 2013; 138(7):2163-70 (Year: 2013).*

(Continued)

*Primary Examiner* — James Choi
(74) *Attorney, Agent, or Firm* — Ulysses John Biffoni (57) ABSTRACT

An apparatus and method to capture aerosols and vapors on substrates from a large variety of sources and matrices for analysis using paper spray mass spectrometry (PS-MS) is disclosed. A holder for a PS cartridge has better direct sampling efficiency, direct capture on substrate, and lower limits of detection thereby improving the collection and analysis of aerosols and vapors. An apparatus and method for aerosol and vapor collection, from both anthropogenic and environmental sources, for example, that is compact and compatible with hand held devices and unmanned vehicles is also disclosed.

11 Claims, 5 Drawing Sheets

(56) References Cited

OTHER PUBLICATIONS

Boone et al., "Aqueous Processing of Atmospheric Organic Particles in Cloud Water Collected via Aircraft Sampling" Environmental Science & Technology 2015 49 (14), 8523-8530 (Year: 2015).*
Orsinia et al., "Refinements to the particle-into-liquid sampler (PILS) for ground and airborne measurements of water soluble aerosol composition" Atmospheric Environment 37 (2003) 1243-1259 (Year: 2003).*
Parshintsev et al., "Particle-into-liquid sampler on-line coupled with solid-phase extraction-liquid chromatography—mass spectrometry for the determination of organic acids in atmospheric aerosols" Journal of Chromatography A, 1217 (2010) 5427-5433 (Year: 2010).*
Chingin, Rapid classification of perfumes by extractive electrospray ionization mass spectrometry (EESI-MS), Rapid Commun. Mass Spectrom. 2008; 22: 2009-2014 (Year: 2008).*

* cited by examiner

DIRECT CAPTURE AND ANALYSIS OF AEROSOLS AND VAPORS BY PAPER SPRAY MASS SPECTROMETRY

CROSS-REFERENCE TO RELATED APPLICATIONS

This application claims the benefit of U.S. Provisional Application No. 62/434,671, filed on Dec. 15, 2016 and entitled "PS-MS for Aerosol Detection and Identification," the complete disclosure of which is hereby incorporated by reference in its entirety.

GOVERNMENT INTEREST

The embodiments described herein may be manufactured, used, or licensed by or for the United States Government.

BACKGROUND

The invention relates generally to the detection and identification of airborne substances and more particularly to capturing aerosols and vapors directly on a substrate or medium for analysis using paper spray mass spectrometry.

Aerosols are colloidal suspensions of fine liquid droplets or solid particulates that are dispersed in air or gas. The particles or droplets can stay airborne for a long time and tend to move in accordance with the direction of air flow. Examples of natural and artificial aerosols include but are not limited to clouds, fog, dust, smoke, diesel exhaust, pollen and particulate air pollutants. Vapors are molecules of various chemicals in the gas phase. A vapor will stay suspended in air indefinitely unless removed, condensed, or trapped. As opposed to aerosols, vapors mostly consist of single, individual molecules moving randomly.

There is a growing need for improved detection, analysis, and identification of aerosols and vapors from a variety of sources. One example is the analysis of aerosolized chemical warfare agents (CWAs), such as those generated by an explosively dispersed chemical munition. Another example is airborne materials present in the environment including both chemicals and molecules of biological origin. There is also increased interest in capturing and identifying biomarkers or drugs of interest that may be present in human exhaled breath, which contains both aerosols and vapors.

Detection of aerosols and vapors can be done using many different technologies. Some of these technologies are primarily directed at the characterization of an aerosol itself such as droplet size, shape, and distribution. Other technologies, such as Light Detection and Ranging (LIDAR), are effective at detecting and tracking large aerosol clouds. However, these technologies typically lack the ability to specifically identify the chemical composition or the concentration of the aerosol or vapor.

In the case of CWAs, detection methods in battlefield and forensic situations can generally be categorized into either onsite direct analysis or capture for later analysis methods. Most onsite or field systems for the detection of aerosolized CWAs prioritize portability and fast analysis times. Examples of this type of system include an IMS-based (ion mobility spectrometry) sensor or colorimetric papers. Although simple to use, IMS sensor devices are unable to directly analyze aerosols. They also have other disadvantages, including sensitivity to temperature and humidity, false alarms due to lack of specificity, and detector saturation from exposure to high concentrations. Another method used in the field, U.S. Army M9 colorimetric papers, only react with a specific class of CWA and tend to have a high false positive rate. Additionally, the analysis of these papers relies on either human visual processing or optical sensors, both of which can be affected by differences in ambient light, color perception, or color blindness. Both of these systems only give qualitative results and are less effective if not completely ineffective at directly identifying or quantifying compounds in aerosolized form.

In contrast to these onsite direct analysis techniques, several approaches have been used to capture an aerosol or vapor for analysis at a later time. These include a variety of filter and sorbent based approaches. After exposure, the filter or sorbent is sent back to an analytical laboratory for processing. This processing typically involves at least a multi-step process of extracting the analyte using either heat or solvents and then identifying a compound in the analyte. The handling process introduces a delay in identification and can also introduce error due to improper handling. Frequently, these capture devices require chromatographic separations, extending analysis time and reducing overall throughput.

Ambient ionization is an analysis technique that uses mass spectrometry without sample preparation or separation. Paper spray mass spectrometry (PS-MS) is an ambient ionization approach in which samples are deposited on a triangular substrate. The substrate is wetted with a solvent, which often includes a charge carrier. A voltage is applied to the substrate, causing a spray of solvent and analyte molecules to emit from a tip of the triangular substrate for analysis. PS-MS has been shown to be highly effective for the detection and quantitation of pharmaceutical drugs, illicit chemicals (both illegal drugs and explosives) and analysis of samples from complex matrices including surfaces, food, blood, urine and tissue. Samples are collected or deposited directly onto a paper substrate from biological and environmental sources and analyzed by MS without the need for desorption or extraction. While PS allows for direct sampling with little to no sample preparation and rapid MS analysis, it has not been used to sample and detect aerosols and vapors.

Thus, a need exists for a system and method to capture aerosols and vapors from a large variety of sources, both anthropogenic and environmental, that requires less sample handling, processing, and extraction prior to analysis by PS-MS. There is a further need for a systematic method that has improved direct sampling efficiency and lower limits of detection by improving the collection of aerosols and vapors, while also maintaining compatibility with analytical techniques including but not limited to mass spectrometry. There is also a need for a system and method for aerosol and vapor collection that is compact and compatible with hand held devices and unmanned vehicles.

SUMMARY

The invention encompasses an apparatus and method for capturing aerosolized compounds with a high sampling efficiency on substrates compatible for analysis by PS-MS. The invention further encompasses a substrate compatible for collection of aerosol or vapor based chemicals, wherein sample atmosphere or air is directed through or at the substrate for collection or exposure, as well as a method for rapidly removing and replacing the substrate for subsequent capture. Furthermore, the substrate is rapidly accessible for PS-MS or other analysis technique.

In an embodiment, the invention encompasses an apparatus for capturing an airborne substance for analysis, including a holder having a rectangular body with an open end, a first opening in a first side adjacent to the open end and a second opening in a second side adjacent to the open end and opposite the first side; and a cap for covering the open end of the holder; a removable cartridge enclosed within the holder, said cartridge including a substrate for capturing the airborne substance; a first fitting operatively coupling tubing from a source of the airborne substance to the first opening; and a second fitting operatively coupling the second opening to a pump for drawing the airborne substance through the holder so that the substrate absorbs the airborne substance.

In a further embodiment, the first opening and the second openings are not aligned.

In another embodiment, the invention encompasses an apparatus for capturing an airborne substance for analysis, including a substrate for capturing the airborne substance; a holder, the holder having a body and a lid that form an enclosed volume for holding the substrate when the lid is attached to the body and a first island having a through-hole and extending into the volume from the lid such that an innermost surface of the first island contacts the substrate; the apparatus further encompassing a first fitting operatively coupling tubing from a source of the airborne substance to the first island and a second fitting operatively coupling the second island to a pump for drawing the airborne substance through the holder so that the substrate absorbs the airborne substance.

In a further embodiment, the body includes a second island having a through-hole operatively coupled to the second fitting and extending into the volume from the body such that an innermost surface of the second island contacts the substrate on the opposite side of the first island.

In another embodiment, the first opening and the second islands are aligned.

In any of the above embodiments, the apparatus is manufactured using an additive manufacturing process.

In any of the above environments, the pump operates at approximately 1 to 5 liters/minute.

In any of the above embodiments, the substrate is analyzed using a mass spectrometer.

In another embodiment, the apparatus includes a cartridge for enclosing the substrate inside the holder.

In any of the above embodiments, the apparatus further includes and is disposed on an airborne platform.

In another embodiment, the invention encompasses a method for capturing an airborne substance for analysis, comprising the steps of preparing a substrate to capture an airborne substance; inserting the substrate into a holder having openings on opposite sides of the substrate after it is inserted into the holder; attaching a pump to one of the openings in the holder; sampling the atmosphere in the region of the substance of interest; and removing the substrate from the holder and analyzing to determine the airborne substance.

In another embodiment, the method includes a step of inserting the substrate into a cartridge after the step of preparing the substrate.

In another embodiment, the removing and analyzing step further comprises the step of analyzing the substrate using paper spray mass spectrometry.

In another embodiment, the step of sampling the atmosphere lasts for approximately 2 minutes.

DESCRIPTION OF THE DRAWINGS

Features of example implementations of the invention will become apparent from the description, the claims, and the accompanying drawings in which:

DETAILED DESCRIPTION

Reference will now be made in detail to one or more embodiments of the invention. While the invention will be described with respect to these embodiments, it should be understood that the invention is not limited to any particular embodiment. On the contrary, the invention includes alternatives, modifications, and equivalents as may come within the spirit and scope of the appended claims. Furthermore, in the following description, numerous specific details are set forth to provide a thorough understanding of the invention. The invention may be practiced without some or all of these specific details. In other instances, well-known structures and principles of operation have not been described in detail to avoid obscuring the invention.

Figure 1:
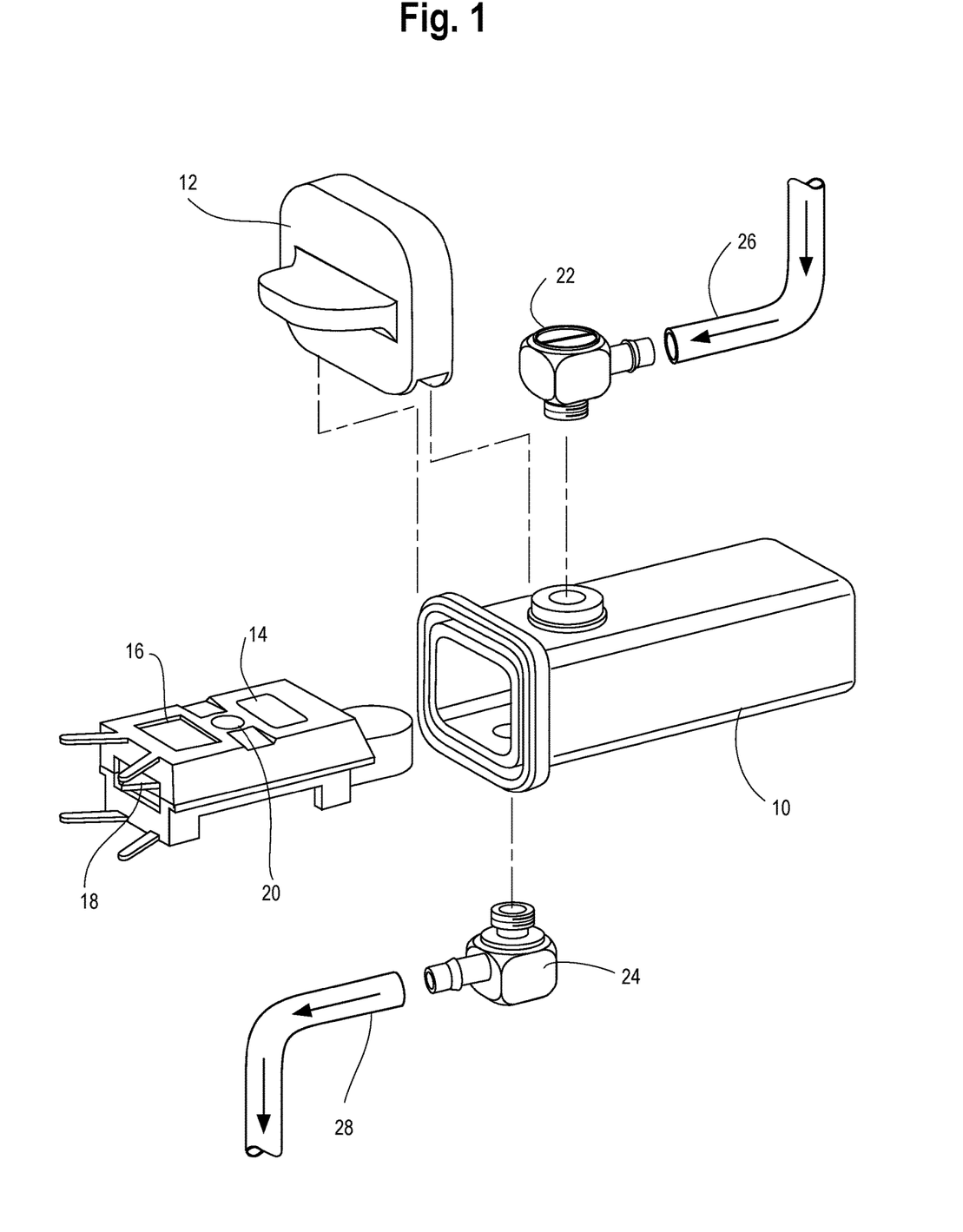
FIG. 1 depicts an exploded perspective view of a holder according to a first embodiment of the present invention.

Turning to FIG. 1, a first embodiment of the invention encompasses a holder 10 and cap 12 for holding a paper spray cartridge 14 during the collection of aerosols or vapors. In an embodiment, cartridge 14 is a Velox Sample Cartridge using the PaperSpray® technology from Prosolia® although any other cartridge capable of holding a substrate could be used. In an alternative embodiment, a substrate may be placed in holder 10 without being enclosed within a cartridge. Cartridge 14 encloses a generally triangular shaped substrate that is used to collect samples through window 16. A tip 18 of the substrate extends from one end of cartridge 14. After sample collection, a voltage is applied at terminal 20 so as to cause an electrospray-like spray to be emitted from tip 18 into a mass spectrometer for analysis. In an embodiment, a paper substrate is used. In an alternative embodiment, other substrates may be used, for example, a glass fiber paper pad. The substrate used for sample collection can be treated in a number of ways to improve the collection of a substance of interest. In an embodiment, a borosilicate glass fiber filter may be treated with a solution of ammonium sulfate and water, then dried. This process may be repeated, or other solutions may be used to treat glass fiber, paper or other substrates, as needed, for collecting a particular substance of interest. In the prior art, paper spray cartridges have only been used for PS-MS analysis by placing liquid samples on the paper substrate for analysis. In contrast, the present invention enables the PS-MS analysis of aerosol or vapor samples collected from air or a gas.

Holder 10 and cap 12 fully enclose cartridge 14 when it is inserted therein. In an embodiment, cap 12 is attached to holder 10 in a sliding motion but it could also be snapped on to the end of holder 10. In addition, a gasket (not shown) could be used to provide a better seal between cap 12 and holder 10. An aerosol or vapor to be analyzed is drawn into holder 10 through tubing 26 and fitting 22 by means of a pump (not shown). It contacts the sample collector substrate inside cartridge 14 through window 16. The aerosol or vapor is then drawn out of cartridge 14 over tip 18 through fitting 24 and tubing 28.

In an embodiment, holder 10 and cap 12 are fabricated with an additive manufacturing technique such as selective laser sintering (SLS) using, for example, glass-filled nylon materials or a thermoplastic material. Other techniques such as injection molding may also be used. Fittings 22 and 24 are right angle barbed fittings. Although a right angle fitting is shown, a straight fitting may also be used. Tubing 26 and 28 are, for example, chemical resistant PVC tubing although other materials such as stainless steel may also be used. A pump, for example, a diaphragm pump (not shown), is used to draw the aerosol or vapor being analyzed through holder 10 in the direction of the arrows shown in FIG. 1. The pump operates at approximately 1.5 L/minute although any suitable pump flow rate may be used.

Figure 2A:
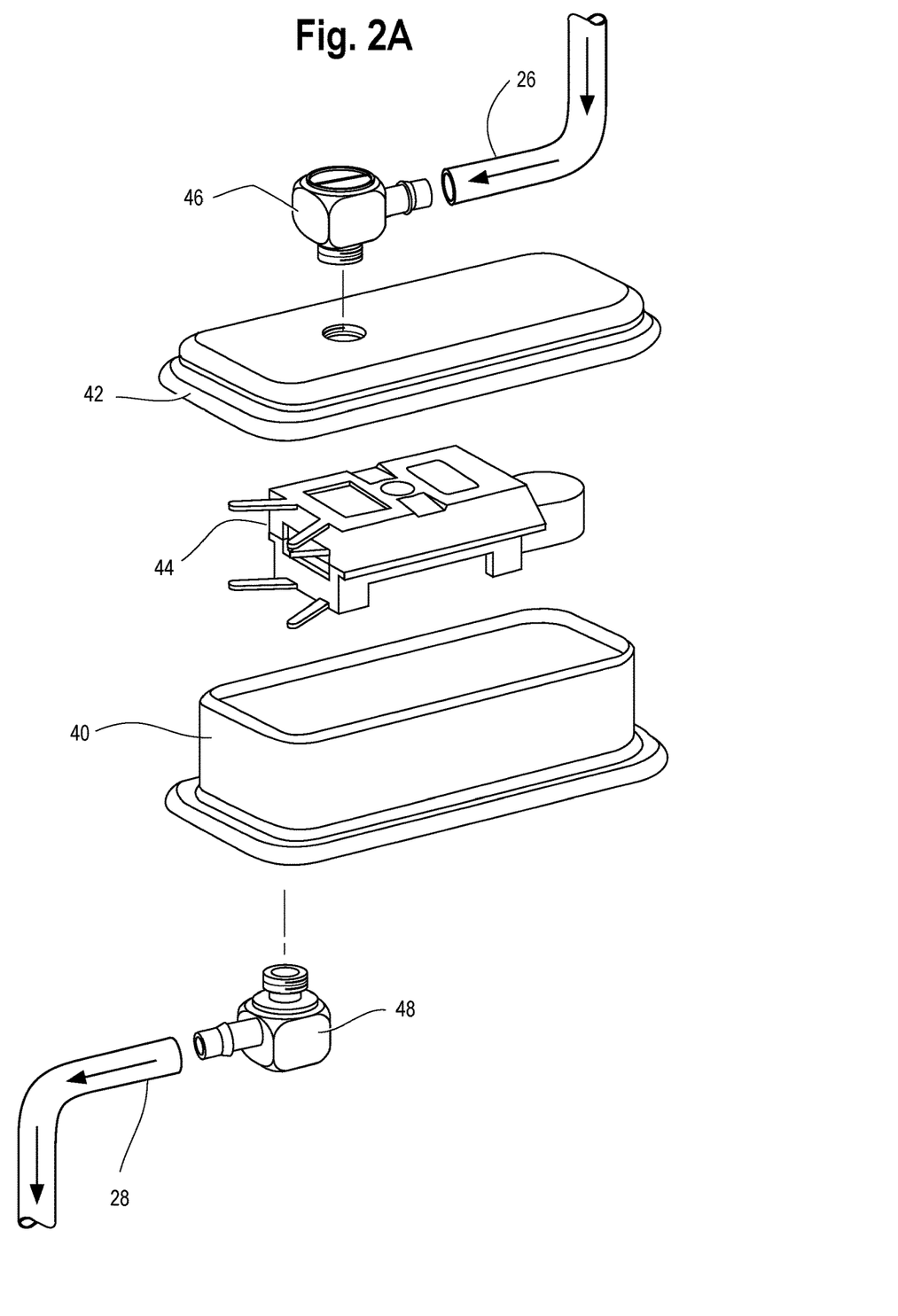
FIGS. 2A and 2B depict exploded and assembled perspective views of a holder according to a second embodiment of the present invention.
Figure 2B:
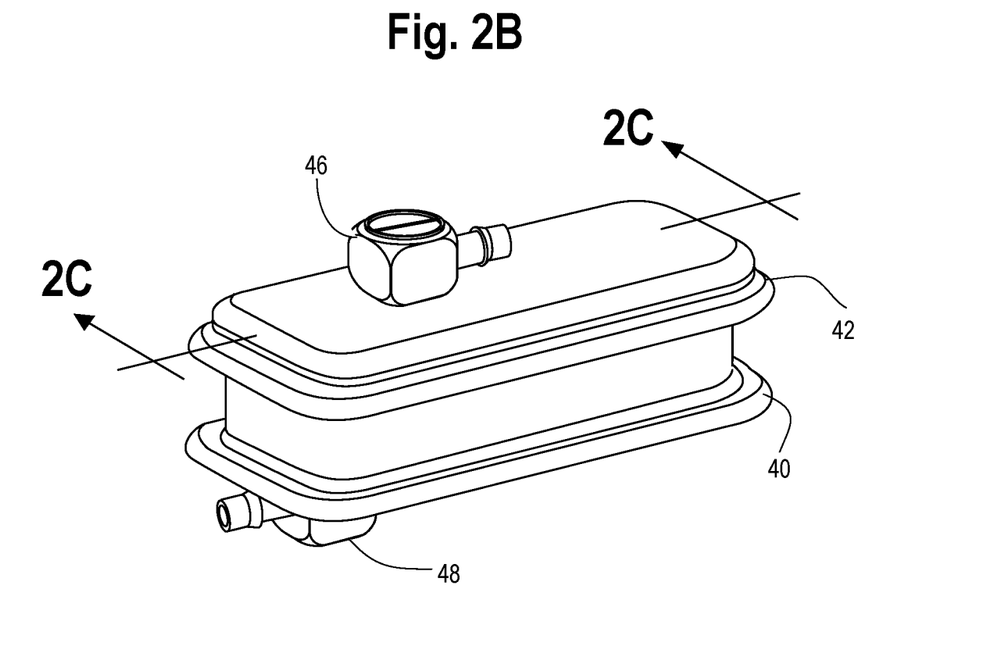
Figure 2C:
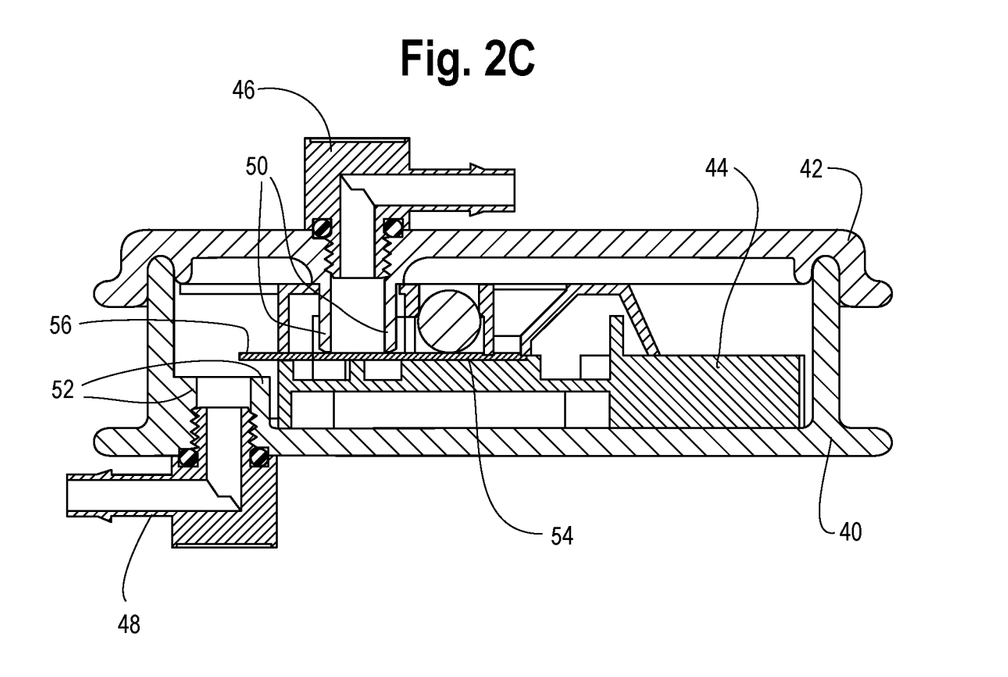
FIG. 2C is a cross sectional view of the embodiment of FIGS. 2A and 2B.

A second embodiment of the invention is shown in exploded view in FIG. 2A and assembled view in FIG. 2B. In this embodiment, holder 40 contains cartridge 44 and is fitted with lid 42. Fittings 46 and 48 are connected to tubing 26 and 28, respectively, and to one or more pumps (not shown) similarly to fittings 22 and 24 of FIG. 1. In both of the embodiments of FIGS. 1 and 2A-2C, the fittings are offset from each other so that a commercial-off-the-shelf cartridge requires no modifications to be compatible with the holder. FIG. 2C shows a cross sectional view of the holder of FIGS. 2A and 2B. Common elements have the same reference numbers. Lid 42 is designed with an island 50 which effectively extends fitting 46 to the surface of the substrate so that the air entering holder 40 through fitting 46 has maximal impact time with substrate 54 to best absorb an aerosol/vapor from an environment being sampled. Offset outlet 52 is incorporated to connect with fitting 48 and thus a vacuum pump (not shown) to draw the air over the tip 56 of substrate 54 inside cartridge 44. The pump operates at approximately 1.5 L/minute although any suitable pump flow rate may be used.

Figure 3A:
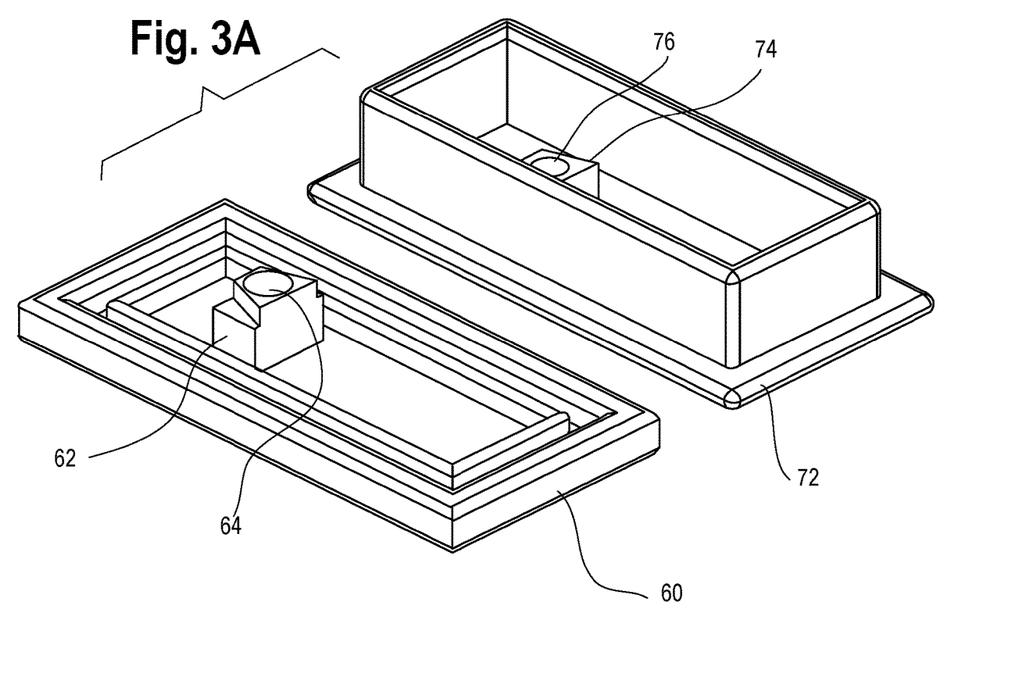
FIGS. 3A and 3B depict exploded and assembled perspective views of a holder and cartridge according to a third embodiment of the present invention.
Figure 3B:
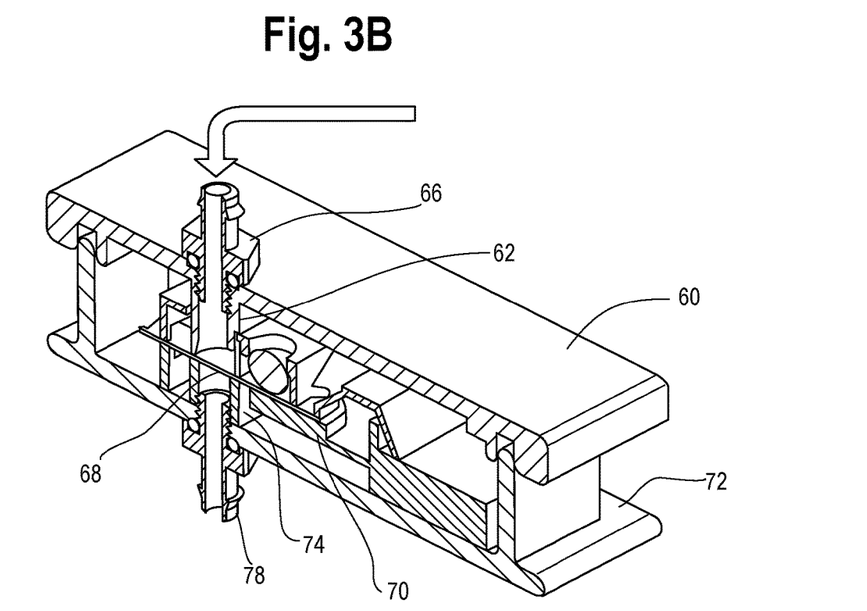

A third embodiment of the invention is depicted in FIG. 3A and FIG. 3B. Similarly to the second embodiment of FIGS. 2A-2C, lid 60 includes a raised island 62 which extends inward perpendicularly from the inner surface of lid 60. It includes through-hole 64 which connects to fitting 66 shown in FIG. 3B. An innermost surface of island 62 will be butted up against the substrate 68 inside a cartridge 70, as discussed above. The third embodiment differs from the second in that holder 72 also incorporates island 74 which extends perpendicularly from the inner surface of holder 72. Island 74 includes through-hole 76 which connects to fitting 78. When lid 60 is attached to holder 72 after cartridge 70 is inserted, islands 62 and 74 are aligned as shown in FIG. 3B. An innermost surface of island 74 butts up against the substrate 68 inside cartridge 70 as discussed in more detail in connection with FIG. 3C.

Figure 3C:
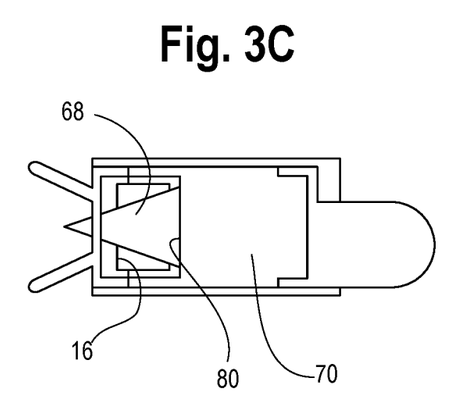
FIG. 3C is a detailed view of a modified paper spray cartridge for use with the embodiment of FIGS. 3A and 3B.

Depending on the cartridge used, it may be necessary to modify it for use in the holder of FIGS. 3A-3B as shown in FIG. 3C. In FIG. 3C, cartridge 70 is modified by creating a window 80 in the plastic housing to allow for the upper 62 and lower 74 islands to seal against the substrate 68. This aspect of the invention uses substrate 68 as a 'seal' to force incoming air through the substrate material to be captured for subsequent PS-MS analysis. As discussed above, the embodiment of FIGS. 3A-3B may also be used with a substrate alone, not enclosed inside a cartridge. In addition, the exact location of islands 62 and 74 may be adjusted to accommodate different cartridge designs.

A cross-sectional view of the assembled holder and lid of FIG. 3A is shown in FIG. 3B. Cartridge 70 is inserted in holder 72 so that when lid 60 is attached, raised islands 62 and 74 contact either side of substrate 68. This provides a more direct path for an aerosol or vapor to contact and be absorbed by substrate 68. Because the aerosol or vapor is being forced through the substrate, a stronger pump (approximately 4.5 L/minute) is used. Although the pump can operate at higher flow rates, since the air is being forced through the material (glass) the actual pumping rate may be significantly reduced (approximately 1.8 L/min).

As explained above, holder 72 and lid 60 are manufactured using an additive manufacturing technique such as SLS, although other techniques such as injection molding could also be used.

Figure 4:
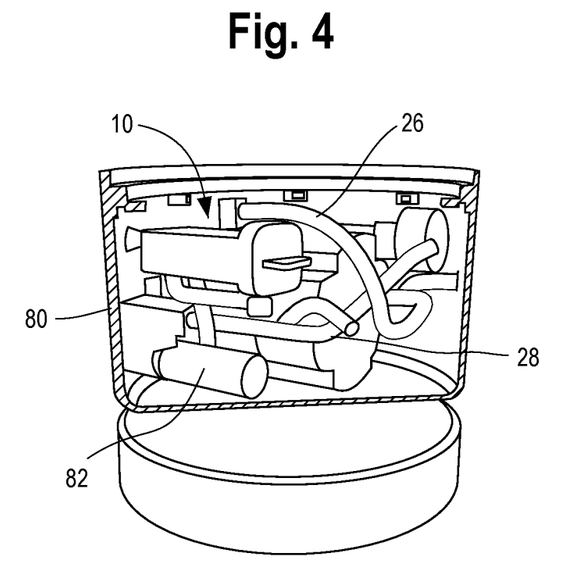
FIG. 4 depicts the holder of FIG. 1 incorporated into a testing platform.

A holder 10 according to a first embodiment of the invention (FIG. 1) as incorporated in a testing platform is shown in FIG. 4. In this example holder 10 is integrated into the ACORNS (Array Configurable of Remote Network Sensors) platform 80 through the use of tubes 26 and 28. FIG. 4 depicts holder 10 integrated with various sensing platforms for environmental monitoring, although any of the above embodiments of the invention may be used. This platform is modular and can provide its own electricity to power all required equipment including diaphragm pumps 82 used to sample air for the holder 10. Although an ACORNS testing platform is shown, any platform capable of providing power and pumping operations may be used.

In all of the above embodiments, an aerosol or vapor is drawn over or through a substrate then analyzed using PS-MS. A method of using the present invention includes preparing a substrate to capture an airborne substance of interest. Optionally, the substrate is inserted into a cartridge. Either the substrate or the cartridge containing the substrate is inserted into a holder and attached to a pumping device. Next the holder is used to sample the atmosphere in the region of the substance of interest. Finally, the substrate or cartridge is removed from the holder for further analysis by PS-MS. In an embodiment, accurate analysis of an environment may be accomplished with approximately two minutes of sampling time, although a variety of sampling times may be used.

If used and unless otherwise stated, the terms "upper," "lower," "front," "back," "over," "under," and similar such terms are not to be construed as limiting the invention to a particular orientation. Instead, these terms are used only on a relative basis. The apparatus in one example comprises any (e.g., horizontal, oblique, or vertical) orientation, with the description and figures herein illustrating one example orientation of the apparatus, for explanatory purposes.

The steps or operations described herein are just for example. There may be many variations to these steps or operations without departing from the spirit of the invention. For instance, the steps may be performed in a differing order, or steps may be added, deleted, or modified.

Although example implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An apparatus for capturing an airborne substance for analysis, comprising:
   a substrate for capturing the airborne substance;
   a holder, said holder further comprising:

a body and a lid that form an enclosed volume for holding the substrate when the lid is attached to the body;

a first island having a through-hole and extending into the volume from the lid such that an innermost surface of the first island contacts the substrate;

an outlet for exhausting air from said body;

a second island having a through-hole operatively coupled to said outlet and extending into the volume from the body such that an innermost surface of the second island contacts the substrate on the opposite side of the first island;

a first fitting operatively coupling tubing from a source of the airborne substance to the first island;

a second fitting operatively coupling the second island to a pump for drawing the airborne substance through the holder so that the substrate absorbs the airborne substance; and a seal formed by the innermost surface of the first island butting up against a top surface of the substrate and the innermost surface of the second island butting up against a bottom surface of the substrate opposite the innermost surface of the first island so that the substrate is compressed between the innermost surface of the first island and the innermost surface of the second island so that all air drawn into said first island through said first fitting flows through the substrate and then into the second island and second fitting and is exhausted through said outlet, so that aerosols and vapors in the air are captured on said substrate.

2. The apparatus of claim 1, wherein the pump operates at approximately 4.5 liters/minute.

3. The apparatus of claim 1, further comprising a cartridge for enclosing the substrate inside the holder.

4. The apparatus of claim 1, wherein said substrate is selected from the group consisting of paper, glass fiber paper pad, and borosilicate glass fiber.

5. The apparatus of claim 1, wherein said apparatus is disposed in or on an airborne platform.

6. The apparatus of claim 1, wherein the substrate is analyzed using a mass spectrometer.

7. A method for capturing an airborne substance for analysis, comprising:

preparing a substrate to capture an airborne substance;

inserting the substrate into a holder, wherein said holder comprises:

a body and a lid that form an enclosed volume for holding the substrate when the lid is attached to the body;

a first island having a through-hole and extending into the volume from the lid such that an innermost surface of the first island contacts the substrate;

an outlet for exhausting air from said body;

a second island having a through-hole operatively coupled to said outlet and extending into the volume from the body such that an innermost surface of the second island contacts the substrate on the opposite side of the first island;

a first fitting operatively coupling tubing from a source of the airborne substance to the first island;

a second fitting operatively coupling the second island to a pump for drawing the airborne substance through the holder so that the substrate absorbs the airborne substance; and a seal formed by the innermost surface of the first island butting up against a top surface of the substrate and the innermost surface of the second island butting up against a bottom surface of the substrate opposite the innermost surface of the first island so that the substrate is compressed between the innermost surface of the first island and the innermost surface of the second island so that all air drawn into said first island through said first fitting flows through the substrate and then into the second island and second fitting and is exhausted through said outlet, so that aerosols and vapors in the air are captured on said substrate;

activating the pump to draw air through the substrate and sampling the atmosphere in the region of the substance of interest; and removing the substrate from the holder and analyzing it by paper spray mass spectrometry to determine the airborne substance.

8. The method of claim 7, wherein the step of sampling the atmosphere lasts for approximately 2 minutes.

9. The method of claim 7, wherein the pump operates at approximately 4.5 liters/minute.

10. The method of claim 7, wherein said substrate is selected from the group consisting of paper, glass fiber paper pad, and borosilicate glass fiber.

11. The method of claim 7, wherein said holder is disposed in or on an airborne platform.

* * * * *